United States Patent [19]
Oneda et al.

[11] Patent Number: 5,447,148
[45] Date of Patent: Sep. 5, 1995

[54] ENDOSCOPIC CONTAMINATION PROTECTION SYSTEM TO FACILITATE CLEANING OF ENDOSCOPES

[75] Inventors: Katsumi Oneda, Alpine; Isao Fujimoto, Cresskill, both of N.J.; Alan D. Lucas, Boston, Mass.

[73] Assignee: Vision Sciences, Inc., Natick, Mass.

[21] Appl. No.: 89,227

[22] Filed: Jul. 8, 1993

[51] Int. Cl.6 .......................... A61B 1/012; A61B 1/005
[52] U.S. Cl. ...................................... 600/131; 600/132; 600/133; 600/158; 600/159
[58] Field of Search .......................... 128/4, 6, 4 A, 917, 128/918, 844

[56] References Cited

U.S. PATENT DOCUMENTS

| Re. 34,110 | 10/1992 | Opie et al. | 128/6 |
|---|---|---|---|
| 4,646,722 | 3/1987 | Silverstein et al. | 128/4 |
| 4,825,850 | 5/1989 | Opie et al. | 128/4 |
| 4,852,551 | 8/1989 | Opie et al. | 128/4 |
| 4,869,238 | 9/1989 | Opie et al. | 128/6 |
| 4,907,395 | 3/1990 | Opie et al. | 53/434 |
| 4,947,827 | 8/1990 | Opie et al. | 128/4 |
| 4,997,084 | 3/1991 | Opie et al. | 206/364 |
| 5,025,778 | 6/1991 | Silverstein et al. | 128/4 |
| 5,193,525 | 3/1993 | Silverstein et al. | 128/4 |
| 5,201,908 | 4/1993 | Jones . | |

FOREIGN PATENT DOCUMENTS

| 1262246 | 10/1989 | Canada | A61B 1/00 |
|---|---|---|---|
| 1305900 | 8/1992 | Canada | A61B 1/00 |
| 1305953 | 8/1992 | Canada | A61B 1/00 |
| 0184778 | 7/1991 | European Pat. Off. | A61B 1/00 |
| 1633964 | 11/1990 | Japan . | |

*Primary Examiner*—Richard J. Apley
*Assistant Examiner*—Beverly A. Meindl
*Attorney, Agent, or Firm*—Seed and Berry

[57] ABSTRACT

A coupling cartridge and end cap for protecting an endoscope from contamination during use. The coupling cartridge provides fluid communication between a pair of external fluid conduits and respective channels formed in an endoscope insertion tube, and between a biopsy channel port projecting from the cartridge and an additional insertion tube channel. In one embodiment, fluid flow through the external fluid conduits is controlled by an external fluid control unit that is electrically controlled by respective switches mounted on the control handle of the endoscope. In another embodiment, fluid flow through the external fluid conduits is controlled by a valve mechanism in the coupling cartridge that is controlled by either an actuator on the cartridge or an actuator on the control handle that is mechanically coupled to the valve mechanism. The coupling cartridge may be removed from endoscope after an endoscopic procedure for disposal or rigorous cleaning. The end cap fits onto the distal end of the insertion tube to isolate it from external contamination. A viewing window, an illumination window, and a biopsy channel project from the distal end of the insertion tube and are received by respective apertures formed in the end cap. The projecting components are tightly surrounded by the end cap as they extend through their respective apertures thereby forming a fluid seal to prevent contamination from reaching the distal end of the insertion tube. A fluid nozzle may also be formed in the end cap to receive a washing fluid from a fluid port at the distal end of the insertion tube and direct the fluid onto the surface of the viewing window for cleaning. A protective sheath may be attached to the end cap and cover the insertion tube to also protect the outer surface of the insertion tube from contamination.

20 Claims, 8 Drawing Sheets

ENDOSCOPIC CONTAMINATION PROTECTION SYSTEM TO FACILITATE CLEANING OF ENDOSCOPES

TECHNICAL FIELD

This invention relates to endoscopes, and more particularly to an endoscope that can be sanitized for future use with relative ease.

BACKGROUND OF THE INVENTION

The use of endoscopes for diagnostic and therapeutic indications is rapidly expanding. To improve performance,, endoscopes have been optimized to best accomplish their purpose. Therefore, there are upper endoscopes for examination of the esophagus, stomach and duodenum, colonoscopes for examining the colon, angioscopes for examining blood vessels, bronchoscopes for examining the bronchi, laparoscopes for examining the peritoneal cavity, and arthroscopes for examining joint spaces. All of these endoscopes have common problems which are addressed by the invention described and claimed herein.

Instruments to examine the rectum and sigmoid colon, known as flexible sigmoidoscopes, are good examples of the usefulness of endoscopes and the need for improvements to make such endoscopes so that they can be easily and quickly cleaned and disinfected. Flexible sigmoidoscopes are expensive, used in a contaminated environment for a procedure which is relatively brief and where problems of cleaning time and contamination are important factors. There has been a large increase in the use of the flexible sigmoidoscope for use in screening symptomatic and asymptomatic patients for colon and rectal cancer. Ideally, flexible sigmoidoscopes must be used rapidly and inexpensively in order to maintain the process of screening at acceptable levels. For example, many clinics would like to perform five to ten sigmoidoscope examinations each hour. One significant problem with making such examinations quick and inexpensive is the time necessary for adequately cleaning the device.

Although endoscopes can be cleaned in about two to four minutes, this relatively cursory cleaning may not be adequate for complete disinfection or sterilization. Even a more complete cleaning requiring on the order of eight to ten minutes may not allow adequate cleaning, particularly in view of the increasing problems with contagious viruses. Even with the use of chemicals such as glutaraldehyde, adequate cleanliness may not always be possible.

While the external surfaces of endoscopes can often be adequately cleaned, endoscopes typically have air, water, biopsy and suction channels extending along their lengths which come into contact with body tissues. Although these channels can be cleaned to some extent, it is very difficult to adequately clean valves for regulating the flow of fluid through these channels as well as various fittings and other components that come into contact with fluids flowing through the channels. If an inexpensive technique could be devised to prevent contamination of these valves, fittings and other components, the difficulty of cleaning endoscopes would not be so acute. For example, if the valves, fittings and channels did not become contaminated, then it would be possible to clean the channels themselves, as well as the external surfaces of the endoscope, with relatively less time and with a much greater degree of assurance that the endoscope is not contaminated by viruses and bacteria after it has been cleaned and disinfected.

Even if endoscopes can be adequately cleaned in eight to ten minutes, the cleaning still prevents endoscopic examinations from being relatively inexpensive. While a physician may spend five to ten minutes performing the endoscopy, he or she will generally waste a great deal of time waiting for the endoscope to be cleaned before he or she can conduct another endoscopic procedure. A partial solution to this "idle time" problem is to purchase multiple instruments so one can be used as the others are being cleaned. However, the expense of having duplicate endoscopes of each type makes this solution impractical, especially for physicians' offices and smaller clinics.

Not only must the idle time of the physician be added to the cost of endoscopy examinations, but the time spent by a nurse or other hospital personnel in the cleaning, as well as the cost of disinfecting chemicals, must be added to the cost of the examination. Although washing machines are available to clean endoscopes, these machines are expensive and not significantly faster than washing by hand. As a result, with conventional endoscopic procedures, both the physician and the relatively expensive endoscope presently have a down time approaching 50%.

One approach to the endoscope contamination problem is described and claimed in U.S. Pat. No. 4,646,722 to Silverstein et al. The Silverstein et al. patent discloses the use of a flexible rubber sheath that surrounds the insertion tube of an endoscope. The distal end of the sheath includes a transparent window that covers the viewing window of an endoscope. The sheath may also include a channel that extends along the insertion tube to allow endoscopic procedures to be performed without contaminating the endoscope itself. Once a procedure has been completed, the sheath, including its channel, is removed from the endoscope thus leaving the endoscope free to perform additional procedures without cleaning or disinfecting. The approach described in the Silverstein et al. patent has provided a great improvement in the ability to conduct endoscopic procedures without either the risk of contamination or the expense of thorough cleaning and disinfecting between procedures. However, the approach described in the Silverstein et al. patent requires a new sheath and channel for each procedure since the sheath is discarded after it used in performing an endoscopic procedure.

One area of conventional endoscopes that is particularly difficult to clean and disinfect is the distal end of the endoscope insertion tube. The distal end of most insertion tubes include not only viewing and lighting windows, but they also include air or water nozzles which, because they are formed by close-fitting surfaces, are very difficult to clean. If a technique could be found to easily clean and disinfect the components mounted at the distal end of the endoscope, as well as the valves for the fluid passages, the remainder of the endoscope could be cleaned and disinfected with relative ease and relatively little expense.

SUMMARY OF THE INVENTION

It is an object of the invention to provide an endoscope that can be cleaned and disinfected with relative ease and relatively little inexpense.

It is another object of the invention to provide an endoscope in which the components of the endoscope that are most difficult to clean and disinfect are disposable.

These and other objects of the invention are provided by a coupling cartridge and a protective end cap that are used with an endoscope of the type having a control handle, an insertion tube extending from the control handle, and a biopsy channel extending through the insertion tube to a biopsy port at the distal end of the insertion tube. The distal end of the insertion tube normally also contains a viewing window, and a lighting window. The inventive coupling cartridge is releasably mounted on the control handle, and it couples a sealed biopsy inlet projecting from the cartridge to the biopsy channel. After an endoscopic procedure has been completed, the coupling cartridge may be removed from the control handle to facilitate cleaning of the endoscope and coupling cartridge. The insertion tube may further include a fluid channel extending from a distal fluid port to a proximal fluid port near the control handle. If so, the coupling cartridge will further include a fluid conduit communicating with a fluid coupler that is in communication with the distal fluid port when said coupling cartridge is mounted on the control handle. The fluid conduit in the cartridge will then be connected to a fluid port on the external fluid control unit. The flow of fluid through the fluid conduit in the coupling cartridge is controlled by either switches on the control handle that control the external fluid control unit or a manually actuatable valve contained within the coupling cartridge.

The protective end cap includes a generally cylindrical flange adapted to fit over the distal end of the insertion tube, and a generally circular end piece mounted in the generally cylindrical flange. The end piece has respective apertures aligned with the viewing window, the lighting window, and the biopsy port. A first sealing mechanism is placed between the cylindrical flange and the distal end of said insertion tube, while a second sealing mechanism is placed between each of the viewing window, the lighting window, and the biopsy channel and their respective apertures. The first and second sealing mechanisms resisting the inflow of contaminants between the end cap and the distal end of the insertion tube. The generally circular end piece may also include a washing nozzle receiving fluid from the fluid port of the insertion tube to wash the surface of the viewing window. The contamination protection system may also include an elongated flexible sheath having one end secured to the generally cylindrical flange. The sheath surrounds the insertion tube to protect the insertion tube from contamination. The viewing window, lighting window, biopsy port, and fluid port preferably are formed at the end of respective bosses that project from the distal end of the insertion tube. The apertures in the generally circular end piece are then shaped to receive the bosses when the end cap is mounted on the insertion tube.

DETAILED DESCRIPTION OF THE INVENTION

Figure 1:
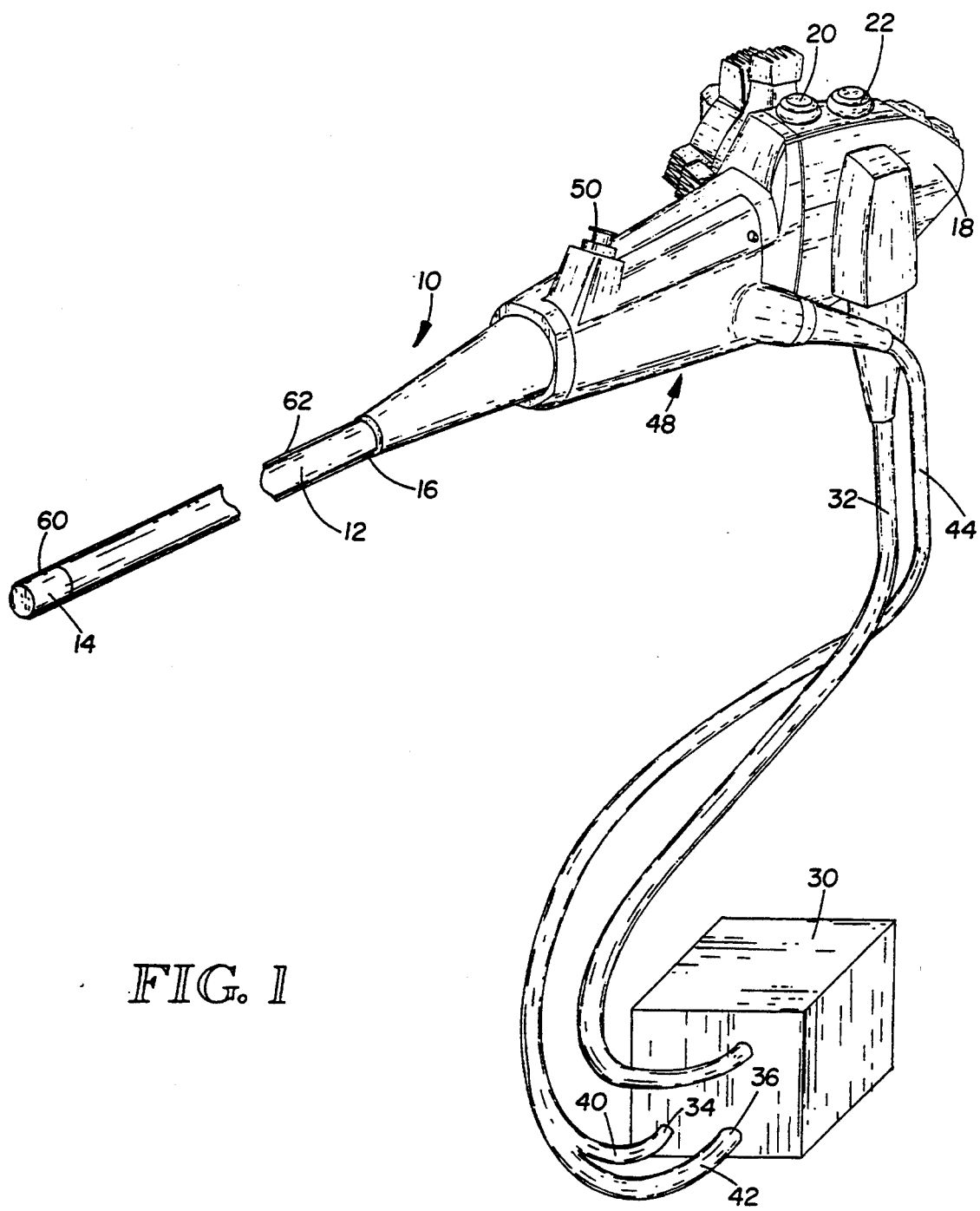
FIG. 1 is an isometric view of an endoscope connected to an external fluid control unit and using the presently preferred embodiment of the inventive contamination protection system.

An endoscope 10 that can be lased with the inventive contamination protection system is illustrated in FIG. 1. The endoscope 10 includes a flexible, elongated insertion tube 12 of conventional design extending from a distal end 14 to a proximal end. 16. The proximal end is attached to a control handle 18 containing a pair of switch actuating buttons 20, 22. The switch actuating buttons 20, 22 are electrically connected to a conventional, external fluid control unit 30 through a cable 32. The cable 32 may also include conventional means for illuminating an illumination window at the distal end 14 of the insertion tube 12 (not shown in FIG. 1). For example, the cable 32 may contain a first fiber optic bundle which couples illumination from the unit 30 through a fiber optic bundle in the insertion tube 12 to an illumination window at the distal end 14.

The wires connected to the switches 20, 22 are coupled to electrically controlled pneumatic valves in the fluid control unit 30. The respective valves are supplied with pressurized water and pressurized air by conventional means, and they communicate with fluid ports 34, 36 on the face of the fluid control unit 30. Respective conduits 40, 42 extend from the fluid ports 34, 36 through a common conduit bundle 44 to a coupling cartridge 48 which clips onto the endoscope control handle 18;. As explained in greater detail below, the coupling cartridge 48 couples, the conduits 40, 42 to respective channels extending through the insertion tube 12, and it also couples a sealed biopsy port 50 of conventional design to a biopsy channel extending through the insertion tube 12.

In operation, after the coupling cartridge 48 has been installed on the control handle 18 and the endoscope 10 has been used to perform an endoscopic procedure, the coupling cartridge 48 is removed from the handle 18. The conduits 40, 42 are then uncoupled from the fluid control unit 30. The conduits 40, 42 and coupling cartridge 48 can then be adequately cleaned in a rigorous cleaning process or they can be discarded to ensure that there is no cross-contamination from one endoscopic procedure to another. By making the coupling cartridge 48 and conduits 40, 42 separable from the endoscope 10, the most difficult to clean components of the endoscope 10 can be either disposable or cleaned more thoroughly than the endoscope 10. The only components of the endoscope 10 that must be cleaned are then the external surface of the insertion tube 12 and the internal channels extending through the insertion tube 12. Significantly, the difficult-to-clean fluid control valves need not be cleaned with the endoscope bull, as mentioned above, can be separately cleaned in a more rigorous procedure or can be disposable.

The inventive coupling cartridge 48 can be used, if desired, with a protective end cap 60 mounted on the distal end 14 of the insertion tube 12. As explained in greater detail below, the isolation cap 60 sealingly engages the insertion tube 12 to isolate the distal end 14 of the insertion tube 12 from bacteria and virus. Significantly, since the cap 60 can be disposable or subjected to a more rigorous cleaning procedure, it is not necessary to clean the difficult-to-clean nozzles and ports with the endoscope. Furthermore, a flexible sheath 62 can surround the insertion tube 12 with its distal end sealed to the cap 60. If the optional sheath 62 is used, it is only necessary to clean the internal channels of the insertion tube 12 since the sheath 62 and cap 60 isolate the external portions of the insertion tube 12 from the environment.

Figure 2:
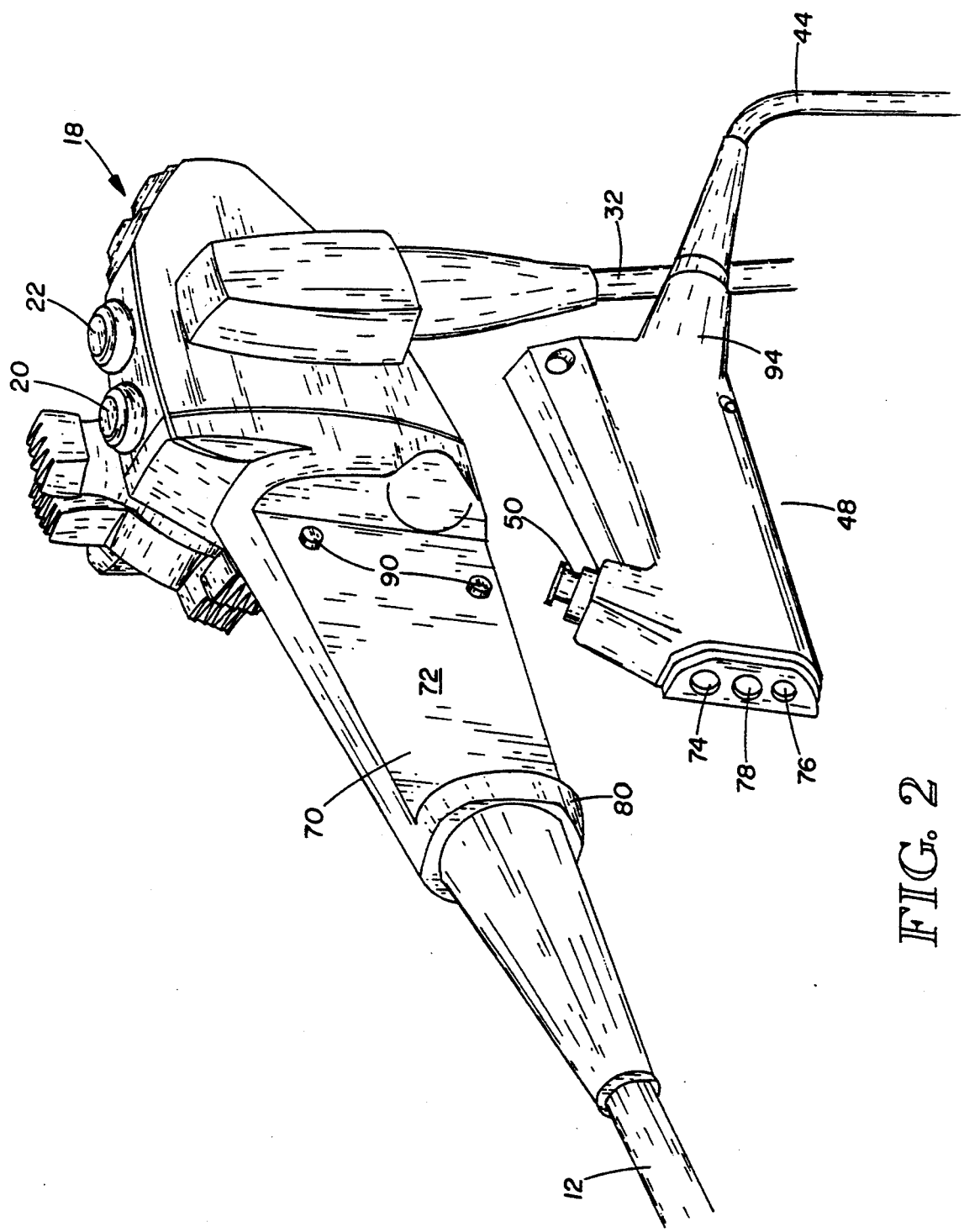
FIG. 2 an isometric view of a portion of the contamination protection system of FIG. 1 shown with its coupling cartridge separated from the endoscope control handle.
Figure 3:
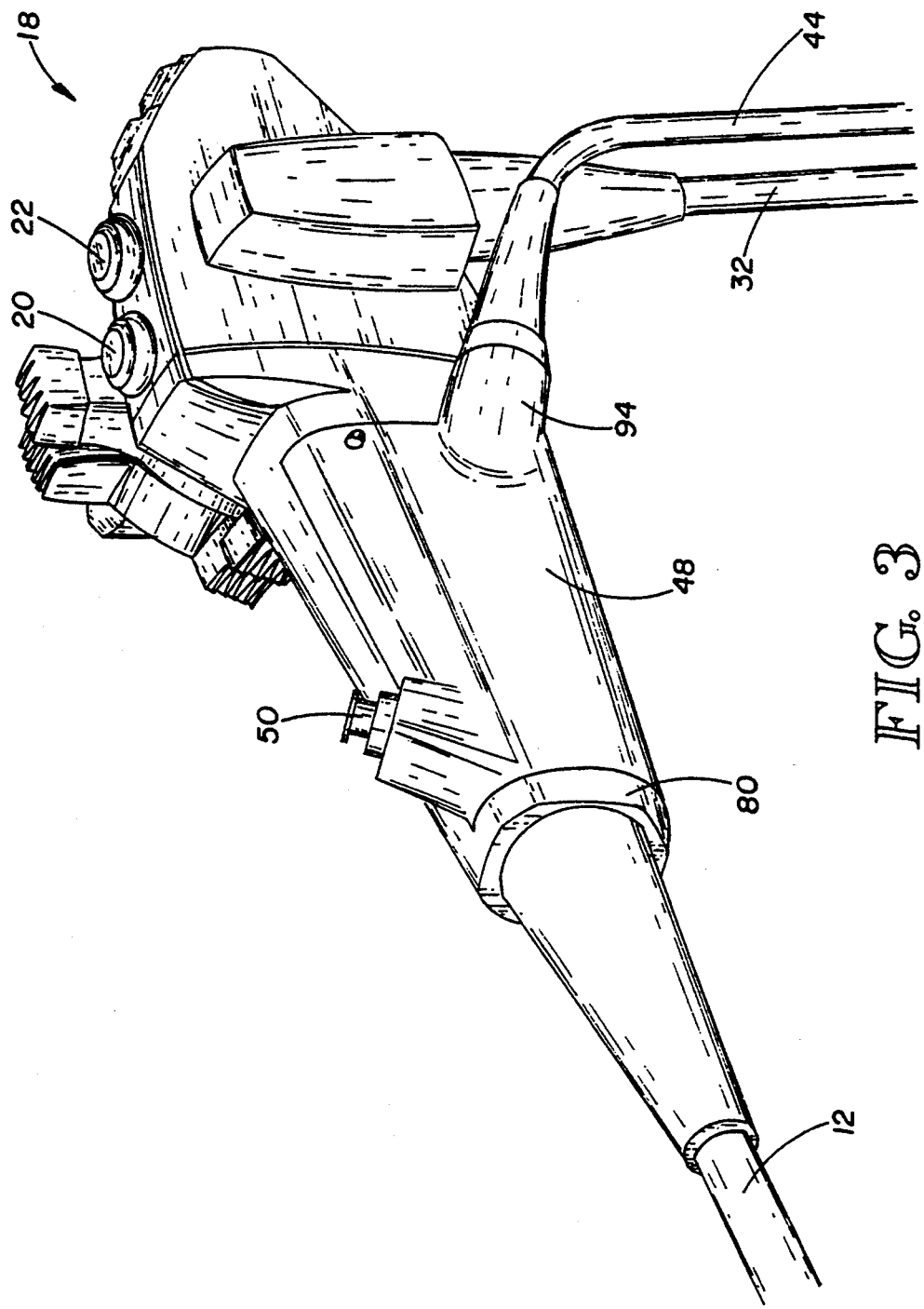
FIG. 3 is an isometric view of the preferred embodiment of FIG. 2 shown with the coupling cartridge clipped onto the endoscope control handle.
Figure 4:
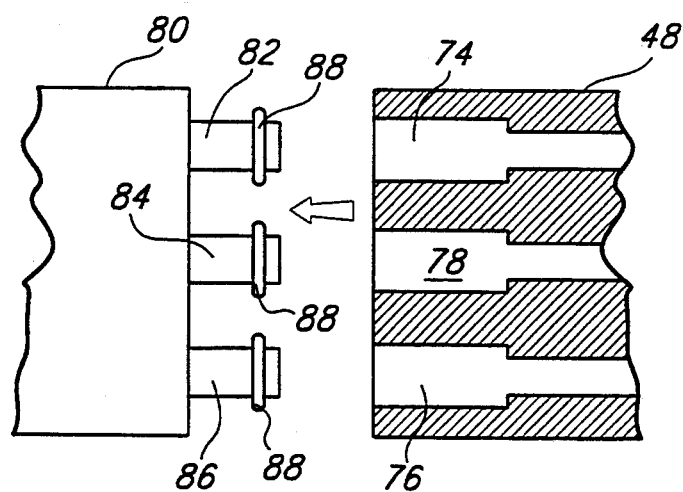
FIG. 4 is a cross-sectional view showing the manner in which the coupling cartridge is in fluid communication of the endoscope.

The coupling cartridge 48 illustrated in FIG. 1 is shown in greater detail in FIGS. 2–4. As best illustrated in FIG. 2, the forward portion 70 of the endoscope control handle 18 has formed therein a cutout 72 having a planar face. The cutout 72 is shaped to receive the coupling cartridge 48 so that when the coupling cartridge 48 is installed on the control handle 18, its outer surface is flush with the outer surface of the control handle 18, as shown in FIG. 3. The forward portion of the coupling cartridge 48 has an air port 74, a water port 76, and a biopsy port 78. The conduits 40, 42 (FIG. 1) communicate through conduit bundle 44 with the air port 74 and the water port 76, respectively. The biopsy port 78 communicates with the sealed biopsy inlet 50.

As illustrated in FIG. 2, a radially outwardly projecting flange 80 is formed in the forward portion 70 of the handle 18 adjacent the insertion tube 12. With further reference to FIG. 4, an air tube 82 projecting rearwardly from the flange 80 communicates with the air channel in the insertion tube 12, a biopsy tube 84 projecting rearwardly from the flange 80 communicates with the biopsy channel of the insertion tube 12, and a water tube 86 projecting rearwardly from the flange 80 communicates with the water channel of the insertion tube 12. Each of the tubes 82–86 is surrounded by a respective O-ring 88.

The coupling cartridge 48 is installed on the handle 18 by inserting the tubes 82–86 into respective ports 76, 80, 78. The cartridge 48 is then pivoted inwardly against the planarr face of the cutout 72 and retained in position by projecting snaps 90 of conventional design which mate with correspondingly positioned recesses (not shown) on the inner surface of the cartridge 48. After an endoscopic procedure has been performed, the cartridge 48 is removed from the handle 18 by pulling outwardly on a rigid transition piece 94 which receives the conduit bundle 44, thereby disengaging the cartridge 48 from the snaps 90. The cartridge 48 is then moved rearwardly to remove the tubes 82–86 from the ports 74, 78, 76, respectively. The cartridge 48 and conduit 44 can then be either disposed of or adequately cleaned in a rigorous cleaning procedure.

Figure 5:
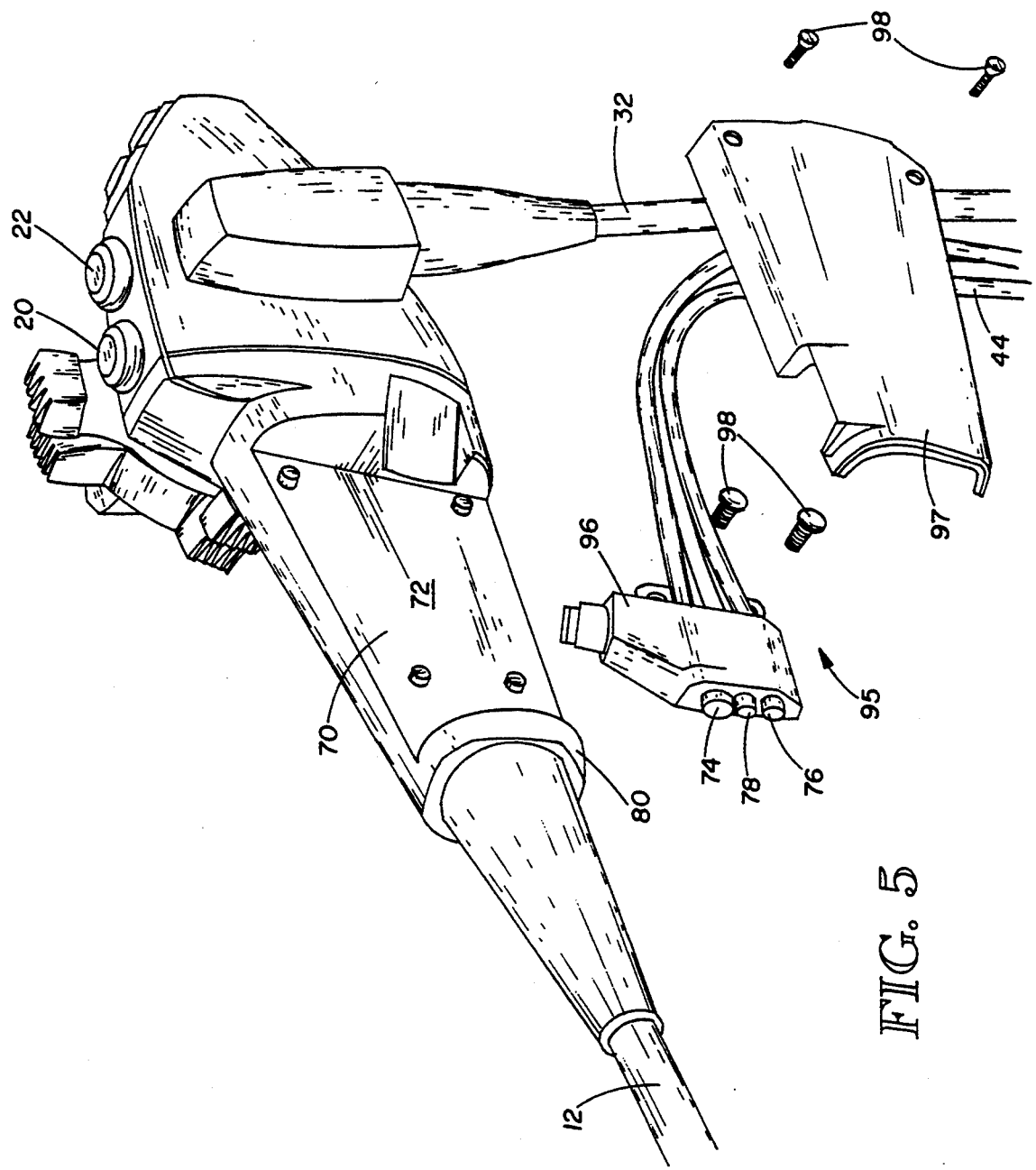
FIG. 5 is an isometric view of an alternative embodiment of a coupling cartridge adapted for mounting on an endoscope control handle.

An alternative embodiment of a coupling cartridge 95 is illustrated in FIG. 5. The coupling cartridge 95 is substantially the same as the coupling cartridge 48 of FIGS. 2–4 except that all of the components described as being in the coupling cartridge 48 are contained in a cartridge body 96 having an overlying cover 97. The cartridge body 96 and cover 97 are each secured to the handle by respective pairs of screws 98.

Figure 6:
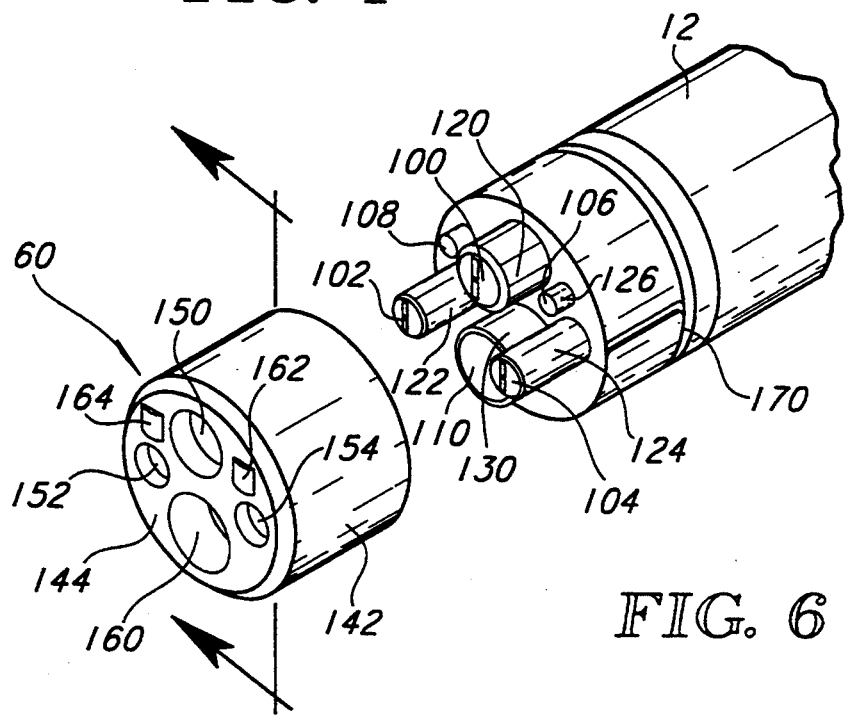
FIG. 6 is an exploded isometric view of a protective end cap adapted for mounting on the distal end of an endoscope insertion tube to protect against contamination.

The use of the coupling cartridge 48 makes it significantly easier to clean the endoscope and provides greater assurances that the endoscope is adequately cleaned prior to performing a subsequent endoscopic procedure. However, as explained above with reference to FIG. 1, for even easier and more thorough contamination protection of endoscopes, the protective end cap 60 illustrated in FIGS. 6–8 can be used along with the coupling cartridge 48. Alternatively, the end cap 60 illustrated in FIGS. 6–8 can be used alone with an endoscope not using a coupling cartridge 48.

As best illustrated in FIG. 1, the preferred embodiment of the protective end cap 60 can be used with an endoscope having an insertion tube 12 terminating at a distal end containing a viewing window 100, a pair of lighting windows 102, 104, an air injection port 106, a water injection port 108, and a biopsy port 110 which communicates with a biopsy channel serving as a working channel. In the presently preferred embodiment, the viewing window 100, illumination windows 102, 104, air channel 106, water channel 108 and biopsy port 110 are each formed at the end of a respective, generally cylindrical boss 120–130.

The preferred embodiment of an end cap 60 includes a cylindrical flange 142 adapted to tightly surround the distal end of the insertion tube 12, and a circular end piece 144 having a viewing aperture 150, a pair of illumination apertures 152, 154 and a biopsy aperture 160. The viewing aperture 150 is sized and positioned to receive the projecting boss 120 of the viewing window 100, the illumination apertures 152, 154 are sized and positioned to receive the projecting bosses 122, 124 of the illumination windows 102, 104, respectively, and the biopsy aperture 160 is sized and position to receive the projecting boss 130 of the biopsy port 110. A pair of nozzles 162, 164 of conventional design are positioned on opposite sides of the viewing aperture 150. The nozzle 162 communicates with the air port 106, while the nozzle 164 communicates with the water port 108. The nozzles 162, 164 direct air or water flowing from the ports 106, 108, respectively, onto the surface of the window 100 when the cap 60 is mounted on the distal end of the insertion tube 12.

An annular groove 170 surrounds the, insertion tube 12 near its distal end. An inwardly projecting ridge 172 is formed on the inner surface of the cylindrical flange 142. When the protective end cap 140 is installed on the insertion tube 12, the groove 170 receives the ridge 172 to lock the cap 140 in position on the insertion tube 12.

Figure 7:
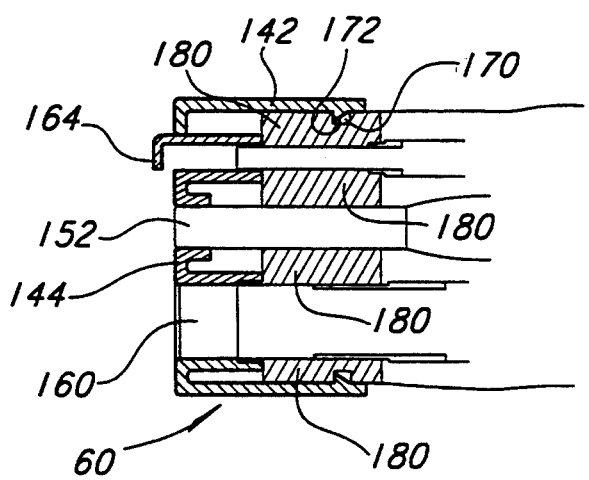
FIG. 7 is a cross-sectional view taken along the line 7—7 of FIG. 6.

As is apparent from FIG. 7, the projecting bosses 126, 128 of the air/water ports 106, 108, respectively, are tightly surrounded by an elastomeric material 180 as they extend through the end cap 60. Similarly, the projecting boss 120 of the viewing window 100 and the projecting boss 130 of the biopsy port 110 are surrounded by the elastomeric material 180. The tight interfit between the elastomeric material 180 and the projecting bosses 120–130 provide a fluid tight seal to prevent contaminants from reaching the distal end of the insertion tube 12. As a result, the protective cap 60 isolates the distal end of the insertion tube 12 from environmental contamination. Significantly, the difficult-to-clean nozzles 162, 164, as well as other portions of the insertion tube 12, remain uncontaminated during use of the endoscope.

Figure 8:
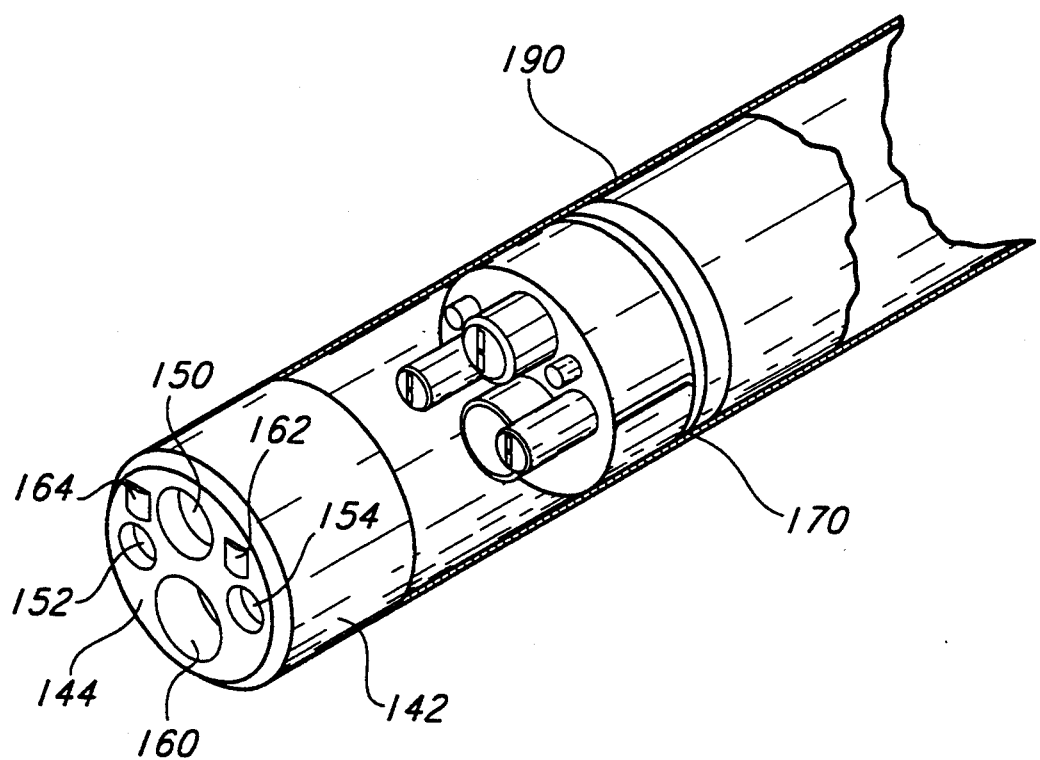
FIG. 8 is an isometric view showing the protective endoscope cap of FIGS. 6 and 7 installed on the distal end of an endoscope insertion tube with an optional protective sheath extending from the cap to cover the insertion tube.

As best illustrated in FIG. 8, the protective end cap 140 may be used with a flexible or resilient sheath 190 of conventional design. The sheath 190 is cylindrical and has a distal end that is secured to the protective cap 40, preferably by being adhesively bonded to the outer surface of the cylindrical flange 142. The sheath 190 has a proximal end (not shown) that terminates near the control handle 18 of the endoscope. When the optional sheath 190 is used, the only portions of the endoscope 10 that become contaminated are the biopsy channel extending from the biopsy port 110, the viewing window 100, the illumination windows 102, 104, and possibly the air and water channels 106, 108, respectively. Significantly, all of these components are relatively easy to clean as compared to the nozzles 162, 164, for example. Further, the end cap 60 and sheath 190 vastly reduce the amount of surface of the insertion tube 12 that can become contaminated.

Figure 9:
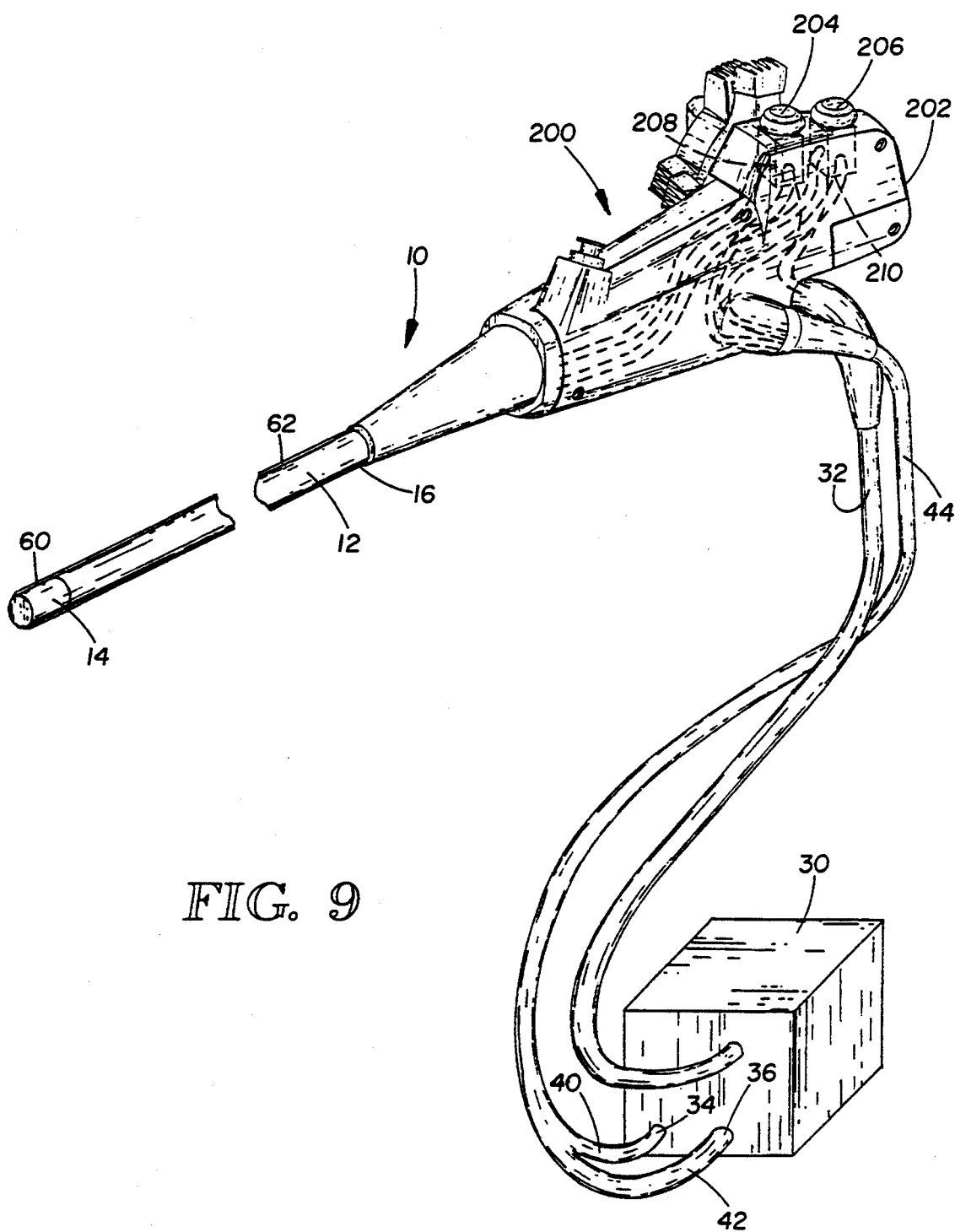
FIG. 9 is an isometric view of an endoscope connected to an external suction and pressurized water source and using an alternative embodiment of the inventive contamination protection system.

As mentioned above, the presently preferred embodiment of the invention illustrated in FIGS. 1-3 uses switches 20, 22 on the control handle 18 to operate valves on an external fluid control device 30 in order to control the flow of fluid through the coupling cartridge 48. However, the flow of fluid through a coupling cartridge can also be controlled directly by valves contained in the cartridge itself. With reference to FIG. 9, a coupling cartridge 200 is mounted on an endoscope 10 that is very similar to the endoscope 10 shown in FIGS. 1-3, and its components have therefore been provided with the same reference numerals. The coupling cartridge 200 differs from the endoscope 48 shown in FIGS. 1-3 in that it has an enlarged rear portion 202 from which valve actuating buttons 204, 206 project. The actuating buttons 204, 206 are mechanically coupled to respective valve mechanisms 208, 210 of conventional design which are well known to one skilled in the art of endoscope design. The valve mechanisms 208, 210 control the flow of fluid from conduits 40, 42, respectively, through the air port 74 (FIG. 5) and the water port 76, respectively. While the valve mechanisms 208, 210 may be somewhat difficult to clean, they may be subjected to a more rigorous cleaning procedure, because they are in the coupling cartridge 200 and may thus be removed from the handle 18. The valve mechanisms 208, 210 in the cartridge 200 may then be given a lengthy treatment with harsh chemicals without damaging the endoscope. Also, the entire coupling cartridge 200, including the valve mechanisms 208, 210, may be made disposable, thus eliminating the risk of cross-contamination from bacteria and viruses that might remain in the valve mechanisms of a conventional endoscope.

Figure 10:
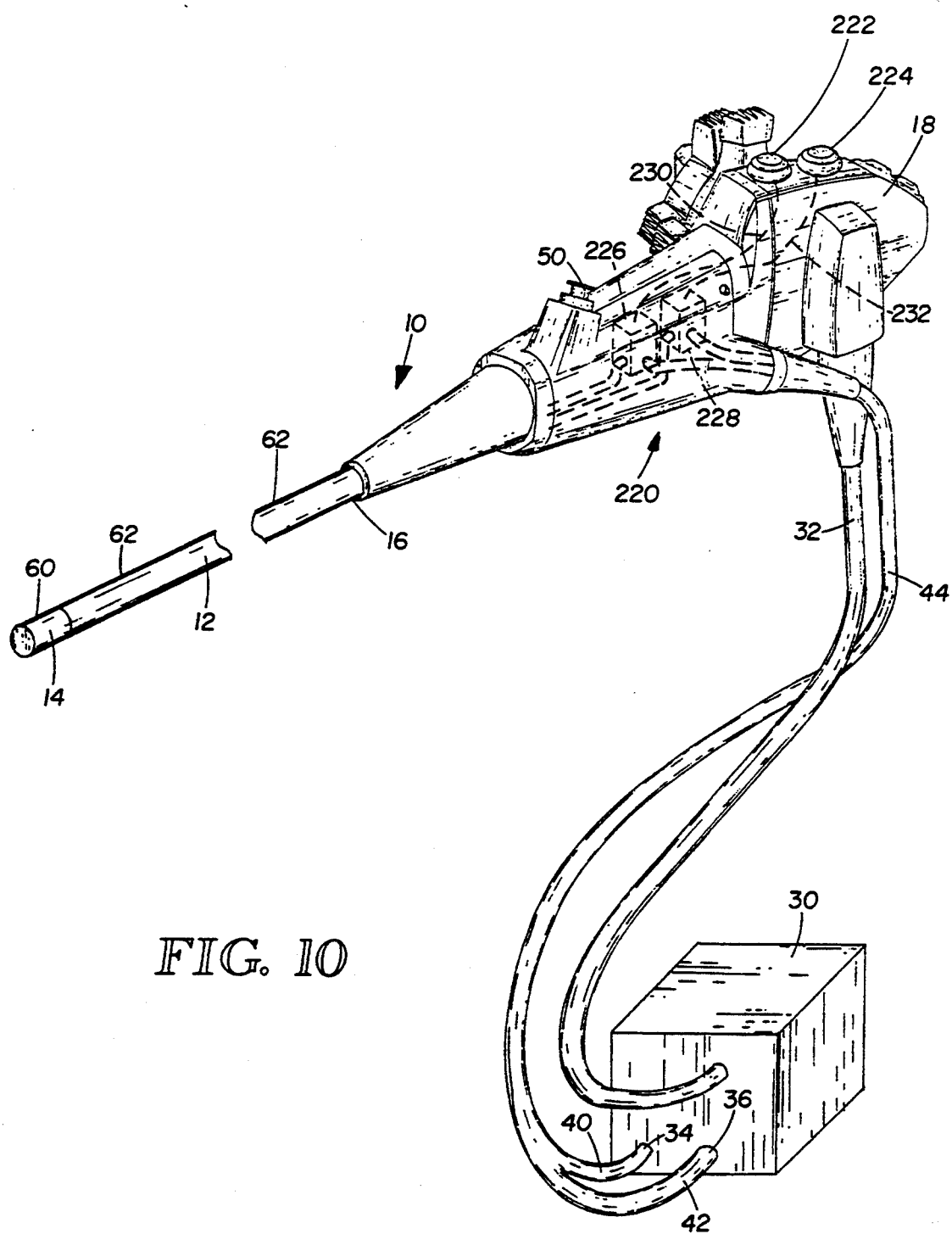
FIG. 10 is an isometric view of an endoscope connected to an external suction and pressurized water source and using still another alternative embodiment of the inventive contamination protection system.

Still another embodiment of the invention is illustrated in FIG. 10. The embodiment of FIG. 10 differs from the embodiment of FIG. 9 in that it uses mechanical valve actuating buttons 222, 224 that are mounted on the control handle 18 itself rather than on the cartridge 200 as in FIG. 9. However, like the embodiment of FIG. 9, the embodiment of FIG. 10 uses valve mechanisms 226, 228 that are mounted within the coupling cartridge 220 itself. The valve mechanisms 226, 228 are operated by the valve actuating buttons 222, 224 through conventional mechanical coupling mechanisms 230, 232 that extend across the interface between the handle 18 and the coupling cartridge 220. By keeping the actuating buttons 222, 224 on the handle 18, the embodiment illustrated in FIG. 10 has the same appearance and feel as a conventional endoscope. However, by mounting the valve mechanisms 226, 228 on the coupling cartridge 220, which can be rigorously cleaned or made disposable, the risk of cross-contamination can be eliminated.

It is thus seen that the inventive coupling cartridge and protective cap can be used either alone or in combination to isolate significant portions of the endoscope from environmental contamination. The coupling cartridge and protective cap thus allow the endoscope to be adequately cleaned with relatively little ease. Although various embodiments of the inventive protection system has been specificallly described, it will be understood that suitable modifications can be made by one skilled in the art without departing from the invention. For example, the contamination protection system has been described for use with an endoscope having a flexible insertion tube. However, the protection system can also be used with scopes having a rigid insertion tube. Also, the number and function of the channels and ports in the insertion tube may vary, and may, of course require corresponding variations in the coupling cartridge and protective end cap. For example, a suction channel may be used instead of the air channel or the water channel. In such case, one of the nozzles 162, 164 simply would be replaced by an aperture. Other variations will be apparent to one skilled in the art.

We claim:

1. An endoscope comprising:
    an endoscope control handle;
    an endoscope insertion tube having a proximal end mounted on said control handle and a distal end containing a viewing window, a lighting window, and a distal biopsy port, said insertion tube further including a biopsy channel extending from said distal biopsy port to a proximal biopsy port adjacent said control handle;
    a coupling cartridge releasably mounted on said control handle, said coupling cartridge having a sealed biopsy inlet in communication with a biopsy channel coupler that communicates with said proximal biopsy port when said coupling cartridge is mounted on said control handle;
    a flange adapted to fit over the distal end of said insertion tube;
    an end piece mounted in said flange, said end piece having respective apertures aligned with said viewing window, said lighting window, and said distal biopsy port;
    a first sealing mechanism between said flange and the distal end of said insertion tube; and
    a second sealing mechanism between each of said viewing window, said lighting window, and said biopsy channel and their respective apertures, said first and second sealing mechanisms resisting the inflow of contaminants between said end cap and the distal end of said insertion tube whereby said coupling cartridge, flange and end piece may be removed from said endoscope control handle after an endoscopic procedure has been completed to facilitate cleaning of said endoscope.

2. The endoscope of claim 1 wherein said control handle has formed therein a recessed portion that receives said coupling cartridge, wherein said proximal biopsy port is formed at the end of a hollow cylindrical boss that projects from said insertion tube into the recessed portion of said control handle, and wherein said biopsy channel coupler is formed by a recess in said coupling cartridge into which said hollow cylindrical boss projects when said coupling cartridge is mounted on said control handle.

3. The endoscope of claim 2 wherein said control handle further includes at least one snap fastener that mates with a snap recess formed in a portion of said coupling cartridge that is spaced apart from the recesses forming said biopsy channel coupler so that said coupling cartridge is releasably retained on said control handle by said snap fastener and the interfit between said cylindrical boss and said coupler.

4. The endoscope of claim 1 wherein said coupling cartridge includes a cartridge body containing said biopsy inlet, and said biopsy channel coupler, said coupling cartridge further including a cartridge cover overlying said cartridge body when said cartridge body is mounted on said control handle, said cartridge cover being secured to said control handle to maintain said control body in position on said control handle.

5. The endoscope of claim 4 wherein said control handle has formed therein a recessed portion that receives said cartridge body, wherein said proximal biopsy port is formed at the end of a hollow cylindrical boss that projects from said insertion tube into the recessed portion of said control handle, and wherein said biopsy channel coupler is formed by a recess in said cartridge body into which said hollow cylindrical boss projects when said coupling cartridge is mounted on said control handle.

6. The endoscope of claim 1, further including an elongated flexible sheath having one end secured to said flange, said sheath extending from said flange to surround said insertion tube thereby protecting said insertion tube from contamination.

7. The endoscope of claim 1 wherein a circumferential groove in formed on said insertion tube near its distal end, and wherein an inwardly projecting ridge is formed on the inner surface of said flange so that said groove receives said ridge when said end cap is mounted on the distal end of said insertion tube whereby said groove and ridge releasably secure said end cap in position on said insertion tube.

8. The endoscope of claim 1 wherein said viewing window, said lighting window, and said distal biopsy port are formed at the end of respective bosses that project from the distal end of said insertion tube, and wherein the apertures in said end piece are shaped to receive said bosses when said end cap is mounted on said insertion tube.

9. The endoscope of claim 1 wherein said endoscope is of the type usable with an external fluid control unit that is operated by switches on an endoscope control handle, wherein said endoscope insertion tube further includes at least one distal fluid port, a proximal fluid port adjacent said control handle, and an endoscope fluid channel extending from said distal fluid port to said proximal fluid port, and wherein said coupling cartridge further includes a fluid conduit in communication with a fluid coupler that communicates with said distal fluid port when said coupling cartridge is mounted on said control handle, said fluid conduit being connected to a fluid port on an external fluid control unit, wherein said control handle further includes at least one manually operable electric switch connected to a control input of said external fluid control unit to control the flow of fluid through the fluid port of said external fluid control unit; and wherein said end piece further includes an aperture aligned with said distal fluid port.

10. The endoscope of claim 9 wherein said end cap further includes a nozzle formed on said end piece in communication with the aperture that is aligned with said distal fluid port, said nozzle facing said the aperture aligned with said viewing window so that a washing fluid flowing through said fluid channel washes the surface of said viewing window when said end cap is mounted on the distal end of said insertion tube.

11. The endoscope of claim 10 wherein said control handle includes at least two manually operable electric switches that are connected to respective control inputs of said external fluid control unit, said control inputs controlling the flow of fluid through a respective fluid port on said external fluid control unit, and wherein said coupling cartridge includes a pair of fluid conduits in communication with respective fluid ports of said external fluid control unit, said fluid conduits communicating with respective proximal fluid ports that communicate with respective fluid channels extending through said insertion tube to respective distal fluid ports at the distal end of said insertion tube.

12. The endoscope of claim 1 wherein said endoscope insertion tube further includes at least one distal fluid port, a proximal fluid port adjacent said control handle, and an endoscope fluid channel extending from said distal fluid port to said proximal fluid port, wherein said end piece further includes an aperture aligned with said distal fluid port, and wherein said a coupling cartridge further includes a fluid conduit in communication with a fluid coupler that communicates with said distal fluid port when said coupling cartridge is mounted on said control handle, and a manually actuatable valve that controls the flow of fluid through said fluid conduit between said fluid coupler and an external fluid port.

13. The endoscope of claim 12 wherein said manually actuatable valve includes a fluid control mechanism contained in said coupling cartridge for controlling the flow of fluid through said fluid conduit between said fluid coupler and said external fluid port, and an actuating member mounted projecting from said control handle and being mechanically coupled to said fluid control mechanism so that the flow of fluid through the fluid conduit in said coupling cartridge is controlled by actuating said actuating member on said control handle.

14. The endoscope of claim 12 wherein said end cap further includes a nozzle formed on said end piece in communication with the aperture that is aligned with said distal fluid port, said nozzle facing said the aperture aligned with said viewing window so that a washing fluid flowing through said fluid channel washes the surface of said viewing window when said end cap is mounted on the distal end of said insertion tube.

15. An endoscope comprising:
an endoscope control handle having formed therein a recessed portion;
an endoscope insertion tube having a proximal end mounted on said control handle and a distal end containing a viewing window, a lighting window, and a distal biopsy port, said insertion tube further including a biopsy channel extending from said distal biopsy port to a proximal biopsy port adjacent said control handle, said proximal biopsy port being formed at the end of a hollow cylindrical boss that projects from said insertion tube into the recessed portion of said control handle; and a coupling cartridge releasably mounted in the recessed portion of said control handle, said coupling cartridge having a sealed biopsy inlet in communication with a biopsy channel coupler that communicates with said proximal biopsy port when said coupling cartridge is mounted in said control handle, said biopsy channel coupler being formed by a recess in said coupling cartridge into which said hollow cylindrical boss projects when said coupling cartridge is mounted in said control handle whereby said coupling cartridge may be removed from said endoscope control handle after an endoscopic procedure has been completed to facilitate cleaning of said endoscope.

16. The endoscope of claim 15 wherein said control handle further includes at least one snap fastener that mates with a snap recess formed in a portion of said coupling conduit that is spaced apart from the recesses forming said biopsy channel coupler so that said coupling cartridge is releasably retained on said control handle by said snap fastener and the interfit between said cylindrical boss and said coupler.

17. An endoscope comprising:
an endoscope control handle having formed therein a recessed portion;
an endoscope insertion tube having a proximal end mounted on said control handle and a distal end containing a viewing window, a lighting window, and a distal biopsy port, said insertion tube further including a biopsy channel extending from said distal biopsy port to a proximal biopsy port adjacent said control handle, said proximal biopsy port being formed at the end of a hollow cylindrical boss that projects from said insertion tube into the recessed portion of said control handle; and
a coupling cartridge body releasably mounted in the recessed portion of said control handle, said coupling cartridge having a sealed biopsy inlet in communication with a biopsy channel coupler that communicates with said proximal biopsy port when said coupling cartridge is mounted in said control handle, said biopsy channel coupler being formed by a recess in said cartridge body into which said hollow cylindrical boss projects when said coupling cartridge is mounted on said control handle; and a cartridge cover overlying said cartridge body when said cartridge body is mounted in the recessed portion of said control handle, said cartridge cover being secured to said control handle to maintain said cartridge body in position in said control handle, whereby said coupling cartridge may be removed from said endoscope control handle after an endoscopic procedure has been completed to facilitate cleaning of said endoscope.

18. An endoscope of the type usable with an external fluid control unit that is operated by a switch on an endoscope control handle, said endoscope comprising:
an endoscope control handle including at least one manually operable electric switch connected to a control input of said external fluid control unit to control the flow of fluid through a fluid port of said external fluid control unit;
an endoscope insertion tube having a proximal end mounted on said control handle containing a proximal fluid port, said insertion tube further including a distal end containing a viewing window, a lighting window, a distal fluid port, and a distal biopsy port, said insertion tube further including a biopsy channel extending from said distal biopsy port to a proximal biopsy port adjacent said control handle, and an endoscope fluid channel extending from said distal fluid port to said proximal fluid port; and
a coupling cartridge releasably mounted on said control handle, said coupling cartridge having a sealed biopsy inlet in communication with a biopsy channel coupler that communicates with said proximal biopsy port when said coupling cartridge is mounted on said control handle, said coupling cartridge further including a fluid conduit in communication with a fluid coupler that communicates with said distal fluid port when said coupling cartridge is mounted on said control handle, said fluid conduit being connected to said fluid port on said external fluid control unit, whereby said coupling cartridge may be removed from said endoscope control handle after an endoscopic procedure has been completed to facilitate cleaning of said endoscope.

19. The endoscope of claim 18 wherein said control handle includes at least two manually operable electric switches that are connected to respective control inputs of said external fluid control unit, each of said control inputs controlling the flow of fluid through a respective fluid port on said external fluid control unit, and wherein said coupling cartridge includes a pair of fluid conduits in communication with respective fluid ports of said external fluid control unit, said fluid conduits communicating with respective proximal fluid ports that communicate with respective fluid channels extending through said insertion tube to respective distal fluid ports at the distal end of said insertion tube.

20. An endoscope comprising:
an endoscope control handle;
an endoscope insertion tube having a proximal end mounted on said control handle containing a proximal fluid port, said insertion tube further having a distal end containing a viewing window, a lighting window, a distal fluid port, and a distal biopsy port, said insertion tube further including a biopsy channel extending from said distal biopsy port to a proximal biopsy port adjacent said control handle; and an endoscope fluid channel extending from said distal fluid port to said proximal fluid port; and
a coupling cartridge releasably mounted on said control handle, said coupling cartridge having a sealed biopsy inlet in communication with a biopsy channel coupler that communicates with said proximal biopsy port and a fluid conduit in communication with a fluid coupler that communicates with said distal fluid port when said coupling cartridge is mounted on said control handle, said coupling cartridge further including a manually actuatable valve that controls the flow of fluid through said fluid conduit between said fluid coupler and an external fluid port, said manually actuatable valve including a fluid control mechanism contained in said coupling cartridge for controlling the flow of fluid through said fluid conduit between said fluid coupler and said external fluid port, and an actuating member projecting from said control handle and being mechanically coupled to said fluid control mechanism so that the flow of fluid through the fluid conduit in said coupling cartridge is controlled by actuating said actuating member on said control handle.

* * * * *